US010095958B2

(12) United States Patent
Tsukada et al.

(10) Patent No.: US 10,095,958 B2
(45) Date of Patent: Oct. 9, 2018

(54) SMOKE DETECTION DEVICE, SMOKE DETECTION METHOD, AND PROGRAM RECORDING MEDIUM

(71) Applicant: NEC Corporation, Minato-ku, Tokyo (JP)

(72) Inventors: Masato Tsukada, Tokyo (JP); Masato Toda, Tokyo (JP); Kenta Senzaki, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 15/125,398

(22) PCT Filed: Mar. 20, 2015

(86) PCT No.: PCT/JP2015/001592
§ 371 (c)(1),
(2) Date: Sep. 12, 2016

(87) PCT Pub. No.: WO2015/146111
PCT Pub. Date: Oct. 1, 2015

(65) Prior Publication Data
US 2017/0116499 A1    Apr. 27, 2017

(30) Foreign Application Priority Data

Mar. 28, 2014    (JP) .................................. 2014-067596

(51) Int. Cl.
G06K 9/46        (2006.01)
G06K 9/66        (2006.01)
(Continued)

(52) U.S. Cl.
CPC ......... G06K 9/6267 (2013.01); G01N 21/538 (2013.01); G01N 21/85 (2013.01);
(Continued)

(58) Field of Classification Search
None
See application file for complete search history.

(56) References Cited

U.S. PATENT DOCUMENTS

2010/0098335 A1* 4/2010 Yamagishi ........... G08B 17/125
                                                    382/168
2012/0140231 A1* 6/2012 Knox .................... G01N 21/53
                                                    356/442
2016/0132714 A1* 5/2016 Pennypacker ....... G08B 17/005
                                                    382/103

FOREIGN PATENT DOCUMENTS

JP      2003-099876 A    4/2003
JP      2008-046017 A    2/2008
JP      2014-006911 A    1/2014

OTHER PUBLICATIONS

Kaiming He, Jian Sun, and Xiaoou Tang, "Single Image Haze Removal Using Dark Channel Prior", IEEE Conference on Computer Vision and Pattern Recognition, (2009).

(Continued)

Primary Examiner — Idowu O Osifade

(57) ABSTRACT

In order to properly detect an outbreak of smoke using a photographic image, this detection device is equipped with an extraction unit, a calculation unit, and a detection unit. By using an image analysis result of an input image, that is, a photographic image captured of a scene under surveillance, the extraction unit generates an image for which a noise component is removed from the input image. By using brightness information contained in the generated image, the calculation unit calculates an attenuation factor of reflected light from a captured object in the input image. The detection unit determines whether an outbreak of smoke is present in the scene under surveillance based on the attenuation factor.

13 Claims, 11 Drawing Sheets

(51) Int. Cl.
| | |
|---|---|
| *G06K 9/62* | (2006.01) |
| *G01N 21/53* | (2006.01) |
| *G06T 5/00* | (2006.01) |
| *G08B 17/12* | (2006.01) |
| *G01N 21/85* | (2006.01) |
| *G06K 9/40* | (2006.01) |
| *G01N 21/17* | (2006.01) |

(52) U.S. Cl.
CPC ............. *G06K 9/40* (2013.01); *G06K 9/4652* (2013.01); *G06K 9/4661* (2013.01); *G06T 5/00* (2013.01); *G06T 5/002* (2013.01); *G08B 17/125* (2013.01); *G01N 2021/1765* (2013.01)

(56) References Cited

OTHER PUBLICATIONS

International Search Report for PCT Application No. PCT/JP2015/001592, dated Jun. 23, 2015.
English translation of Written opinion for PCT Application No. PCT/JP2015/001592.

\* cited by examiner

SMOKE DETECTION DEVICE, SMOKE DETECTION METHOD, AND PROGRAM RECORDING MEDIUM

This application is a National Stage Entry of PCT/JP2015/001592 filed on Mar. 20, 2015, which claims priority from Japanese Patent Application 2014-067596 filed on Mar. 28, 2014, the contents of all of which are incorporated herein by reference, in their entirety.

TECHNICAL FIELD

The present invention relates to a technique to detect that smoke is generated based on an image capturing an indoor-outdoor scene.

BACKGROUND ART

Smoke generated by fire is one of aerosols, and is an air mass containing fine particles generated by incomplete combustion. Generally, smoke generated when combusting a substance containing cellulose (carbohydrate that makes up a third of natural vegetable materials and exists in the largest amount on earth), such as wood and paper, as a major ingredient often has a white color. The white smoke tends to generate in the early phase of fire, for example. It is important from the viewpoint of disaster prevention to early detect the white smoke generated in the early phase of fire and lightly dispersed into the air.

PTL 1 discloses a detection device that detects that smoke is generated, by performing image processing of an image captured with a camera (captured image). The detection device described in PTL 1 has configuration for calculating predetermined two or more smoke detection determination elements in a predetermined detection region in the captured image. The detection device detects that smoke is generated using the calculated smoke detection determination elements. Furthermore, the detection device has configuration for detecting that the smoke is black smoke, and has a function to issue an alarm when detecting that black smoke may be generated. Furthermore, the detection device determines breakout of fire based on the number of times of continuous detection of smoke or the like, and has a function to issue a warning when determining that fire breaks out.

NPL 1 discloses a technique for removing fog and mist from a captured image. Furthermore, the following is described in NPL 1. More specifically, when a real scene (actual landscape or the like) is captured by a camera, observation light captured with the camera is mixed light in which reflected light and environment light are mixed. The term reflected light here is light reflected by a captured object. The environment light is indirect light diffused (scattered) by objects, atmosphere, and the like.

The intensity (brightness) I of the observation light can be expressed as the formula (1).

$$I = (1-\omega) \times J + \omega \times A \quad (1)$$

Here, in the formula (1), J represents the intensity (brightness) of the reflected light, and A represents the intensity (brightness) of the environment light. The intensity A of the environment light can be calculated by a calculation method that is not described here. In addition, w represents a superimposing rate of the environment light (a rate of the environment light included in the observation light). When smoke appears in the captured image, the superimposing rate w of the environment light becomes a higher value compared to when smoke does not appear, or an image region in which smoke does not appear. Accordingly, the superimposing rate w is evaluated using the observation light captured by the camera, and it is determined that smoke is generated (appears) when the superimposing rate w exceeds a threshold value.

CITATION LIST

Patent Literature

[PTL 1] Japanese Patent Application Laid-open Publication No. 2008-046017

Non Patent Literature

[NPL1] Kaiming He, Jian Sun, and Xiaou Tang, "Single Image Haze Removal Using Dark Channel Prior", IEEE Conference on Computer Vision and Pattern Recognition, (2009)

SUMMARY OF INVENTION

Technical Problem

The detection device described in PTL 1 can issue the alarm when determining that black smoke may be generated, and moreover, can issue the warning when detecting that fire breaks out. However, the detection device does not issue the alarm and the warning until a predetermined condition is satisfied, and thus, cannot report an initial state of fire. Therefore, there is a problem in that, even when the warning is issued, it is difficult for a building manager who has listened the warning, for example, to stop the fire from spreading.

In addition, in the technique described in NPL 1, an index corresponding to the superimposing rate of the environment light or an attenuation factor of light (attenuation factor=1−superimposing rate) needs to be calculated with high accuracy so as to detect smoke indicating breakout of fire based on the captured image with the camera. However, generally, noise is included in the captured image with the camera, and the index cannot be calculated with high accuracy due to the noise, and thus, it is difficult to appropriately detect generation of smoke in the technique of NPL 1. Therefore, it is difficult to stop fire from spreading even if the technique of NPL 1 is used.

The present invention was conceived so as to solve the above-described problems. More specifically, it is a main object of the present invention to provide a technique to appropriately detect that smoke is generated using a captured image.

Solution to Problem

To achieve the main object of the present invention, a detection device of the present invention includes:

an extraction unit that, by using a result of an image analysis of an input image that is a captured image obtained by capturing a scene to be monitored, generates an image obtained by removing a noise component from the input image;

a calculation unit that, by using brightness information included in the image generated by the extraction unit, calculates an attenuation factor of reflected light from an object captured in the input image; and a detection unit that determines whether smoke is generated in the scene to be monitored based on the attenuation factor.

A detection method of the present invention includes:

by using a result of an image analysis of an input image that is a captured image obtained by capturing a scene to be monitored, generating an image obtained by removing a noise component from the input image;

by using brightness information included in the generated image, calculating an attenuation factor of reflected light from an object captured in the input image; and determining whether or not smoke is generated in the scene to be monitored based on the attenuation factor.

In a program recording medium storing a computer program of the present invention, the computer program makes a computer execute:

by using a result of an image analysis of an input image that is a captured image obtained by capturing a scene to be monitored, generating an image obtained by removing a noise component from the input image;

by using brightness information included in the generated image, calculating an attenuation factor of reflected light from an object captured in the input image; and determining whether smoke is generated in the scene to be monitored based on the attenuation factor.

It is to be noted that the main object of the present invention is also achieved by the detection method of the present invention corresponding to the detection device of the present invention. Furthermore, the main object of the present invention is also achieved by the computer program relating to the detection device and the detection method of the present invention, and the program recording medium storing the computer program.

Advantageous Effects of Invention

The present invention can appropriately detect that smoke is generated using a captured image.

DESCRIPTION OF EMBODIMENTS

Hereinafter, exemplary embodiments according to the present invention will be described with reference to the drawings.

First Exemplary Embodiment

Figure 1:
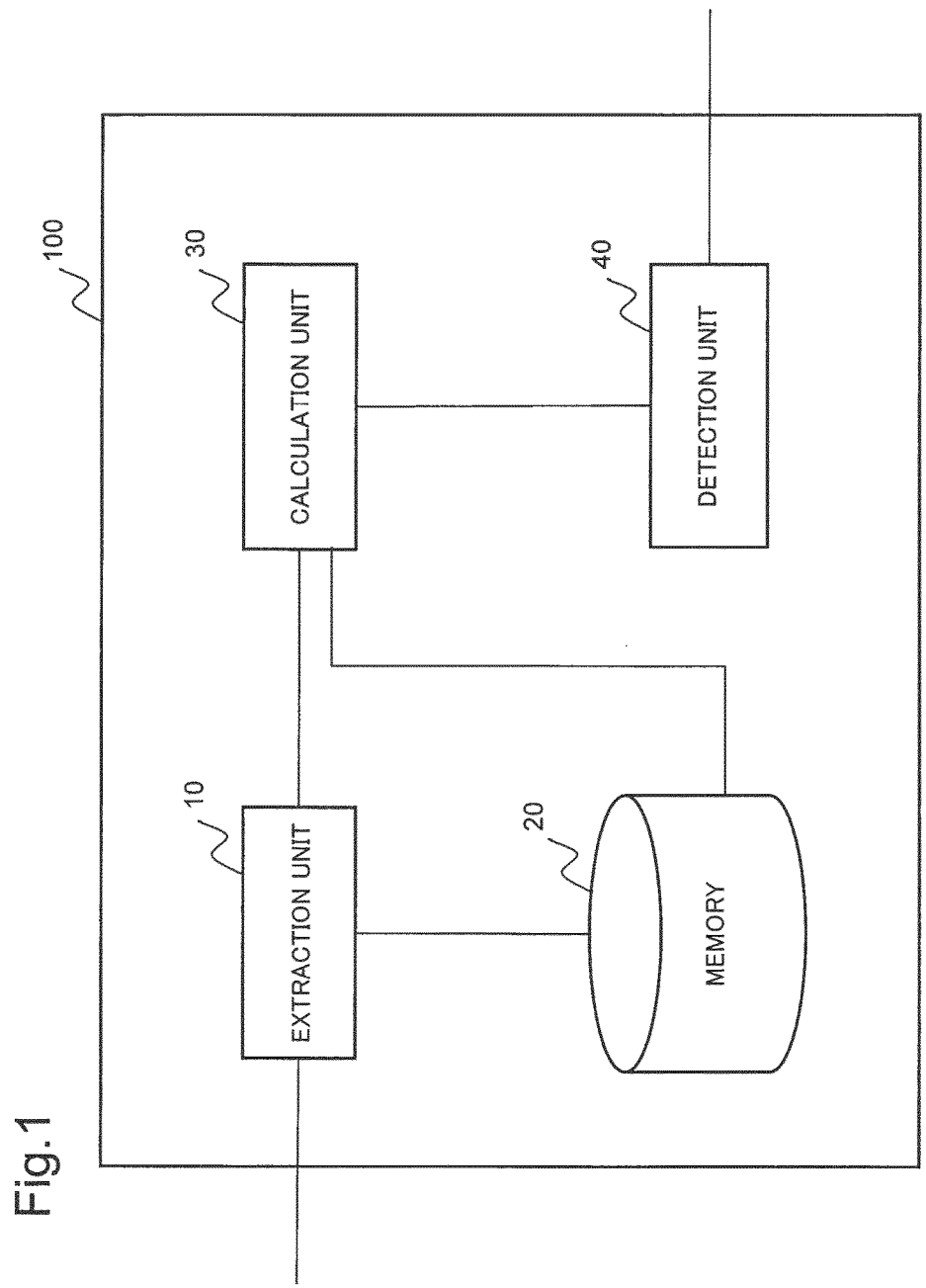
FIG. 1 is a block diagram simply illustrating a configuration of a detection device of a first exemplary embodiment according to the present invention.
Figure 2:
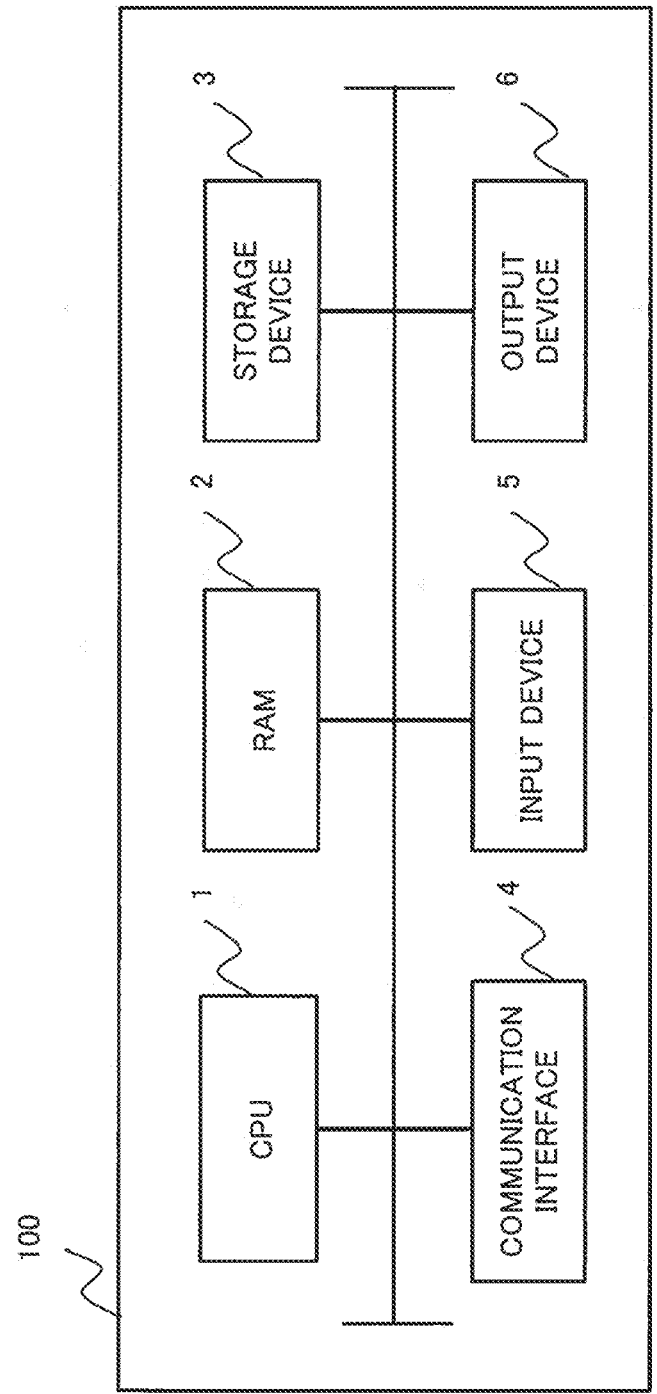
FIG. 2 is a block diagram illustrating a configuration example of a computer that achieves the detection device of the first exemplary embodiment.

FIG. 1 is a block diagram simply illustrating a functional configuration of a detection device of a first exemplary embodiment according to the present invention. As illustrated in FIG. 1, a detection device 100 of the first exemplary embodiment includes an extraction unit 10, a memory 20, a calculation unit 30, and a detection unit 40, as function unit. FIG. 2 is a block diagram illustrating a hardware configuration that achieves the detection device 100. As illustrated in FIG. 2, the detection device 100 has a CPU (Central Processing Unit) 1, a RAM (Random Access Memory) 2, a storage device 3, a communication interface 4, an input device 5, and an output device 6, for example.

The storage device 3 is a storage medium, such as an optical disk device, a magnetic disk device, and a semiconductor memory, and has a function to store various types of computer programs (hereinafter, sometimes also referred to as programs) and various types of data, for example. The CPU 1 reads the program from the storage device 3, and writes the read program into the RAM 2. The CPU 1 can execute various functions by operating in accordance with a control procedure expressed in the program stored in the RAM 2. In the first exemplary embodiment, the extraction unit 10, the calculation unit 30, and the detection unit 40 are achieved by the CPU 1. In addition, a function (operation) of the extraction unit 10 and the detection unit 40 to communicate information with the outside is achieved by execution of an OS (Operating System) program by the CPU 1, for example. Furthermore, the memory 20 is achieved by the RAM 2 or the storage device 3, for example.

The communication interface 4 has a function to communicably connect the CPU 1 to a network or an external storage medium. The CPU 1 sometimes retrieves external data by the communication interface 4. The input device 5 is a device with which a user inputs information to the detection device 100, and is configured by a keyboard, a mouse, or a touch panel, for example. The output device 6 is a device that presents information to the user, and is configured by a display, for example. It is to be noted that the hardware configuration illustrated in FIG. 2 is merely an example of a hardware configuration that achieves the detection device 100, and the extraction unit 10, the calculation unit 30, and the detection unit 40 illustrated in FIG. 1 may be separately configured by independent logic circuits, for example.

Next, the function units 10 to 40 in the detection device 100 will be described.

Figure 3:
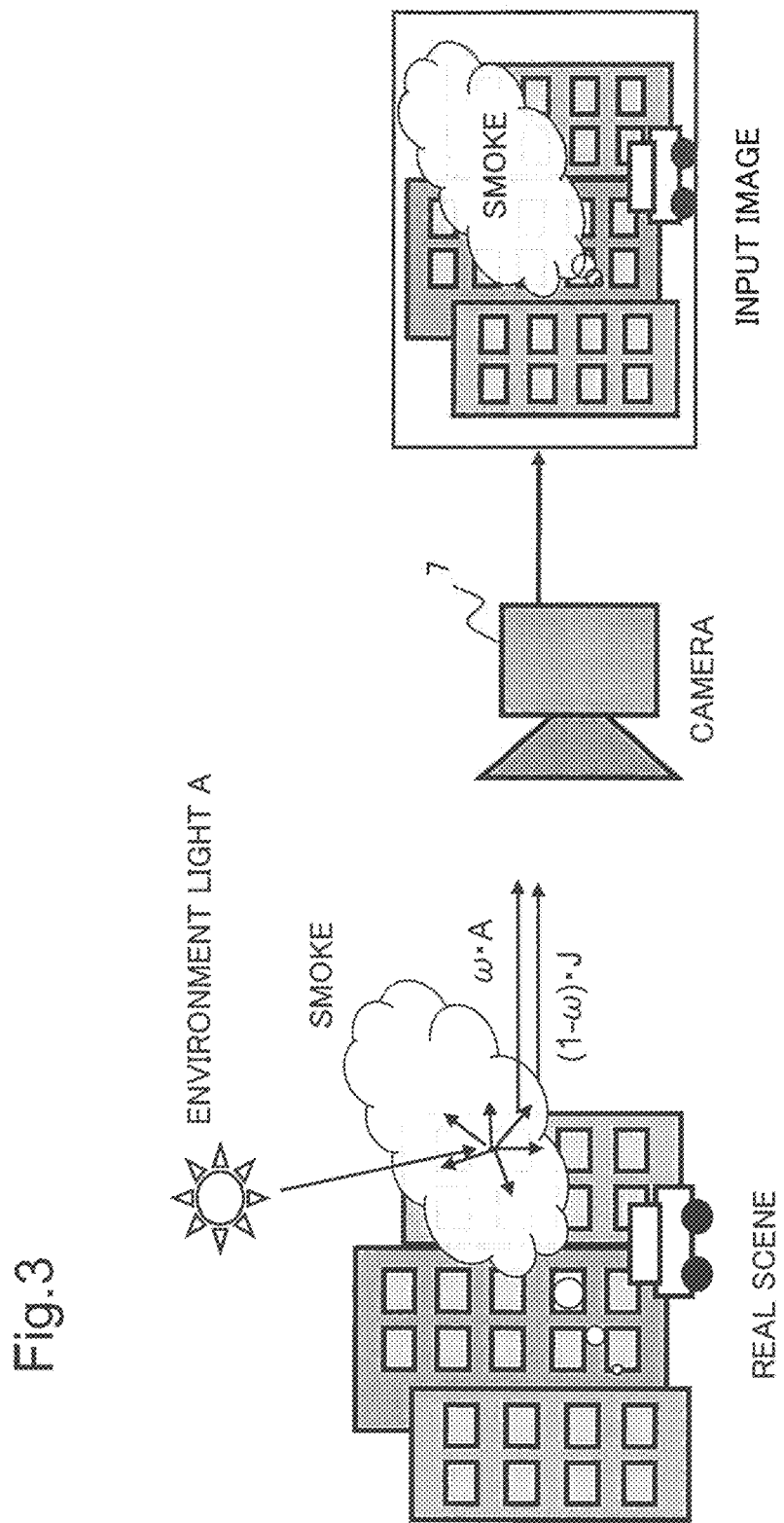
FIG. 3 is a diagram illustrating an example of a captured image with a camera.

A captured image of a real scene captured with an imaging device 7 such as a camera illustrated in FIG. 3 is inputted to the extraction unit 10. The extraction unit 10 has a function, when the captured image is inputted, to perform image processing of an input image that is the inputted captured image and analyze the input image regarding a visual characteristic. The term visual characteristic here represents a frequency characteristic in human vision (for example, contrast sensitivity function), for example. This is a characteristic in which sensitivity is high in a visible light frequency range and low in a high-frequency range and a low-frequency range.

The extraction unit 10 has a function to extract a skeleton component from the input image using the analysis result. The skeleton component of an image is information representing a comprehensive structure, such as color and brightness, in each of segmented regions (for example, pixels) of the input image segmented into multiple regions. The extraction unit 10 generates a skeleton image based on the extracted skeleton component.

As a method for extracting the skeleton component from the input image, for example, application of a method of total variation norm minimization is conceivable. The total variation norm minimization is a technique to remove a vibrational component included in a pixel value of each of pixels in an image as a texture component or a noise component, and is a method capable of extracting information of brightness and color of each of segmented regions (for example, pixels) in the input image. In the first exemplary embodiment, for example, a total variation norm is minimized using a subgradient method, for example. The subgradient method is a method for performing optimization using subdifferential, for example.

When using the total variation norm minimization method, the extraction unit 10 extracts the skeleton component from the input image by solving a formula of a minimization problem expressed by a formula (2) in the input image, for example. The formula (2) is a formula representing that a formula in which a regularization term (the second term of the formula (2)) is introduced into the total variation norm (the first term of the formula (2)) is minimized.

$$\min_{B}\left(\int |\nabla B| dxdy - \frac{\mu}{2}\|I-B\|_2^2\right) \quad (2)$$

Here, in the formula (2), ∇B represents vector differential (gradient) of the skeleton component B. x, y are parameters representing a coordinate value of a pixel in the image. μ is a parameter that maintains the fidelity to the original image (input image), and a value corresponding to an element related to the quality of the captured image (for example, performance of camera, or imaging environment) is given in advance.

It is to be noted that, when using the total variation norm minimization method, the following processing may be performed. More specifically, the extraction unit 10 analyzes the input image at a plurality of resolutions (multiresolution analysis), and extracts the skeleton component by the total variation norm minimization method based on each of the analysis results. When extracting the skeleton component in this manner, the extraction unit 10 can remove the fine vibrational component, and can also remove vibration having a wide period (low-frequency vibration) that influences the image, so that a higher-accuracy skeleton component can be obtained.

The extraction unit 10 stores information of the generated skeleton image in the memory 20. It is to be noted that the information of the skeleton image is a set of the skeleton components B of the respective pixels in the input image. Here, the skeleton component B of each of the pixels is also referred to as B(p, λ). It is to be noted that p represents a coordinate position of each of the pixels. λ represents information that distinguishes color channels (red channel, green channel, blue channel, and the like).

It is to be noted that the method for minimizing the total variation norm is not limited to the subgradient method, and Chambolle's projection method (hereinafter, referred to as projection method) may be used, for example. The projection method is a method using a semi-implicit steepest descent method, for example.

The calculation unit 30 has a function to calculate an attenuation factor of light in the pixel at the coordinate position p using the skeleton component B(p, λ) extracted by the extraction unit 10, that is, the color information and the brightness information included in the skeleton image generated by the extraction unit 10. The term attenuation factor here indicates the degree of attenuation of reflected light due to smoke generated by fire or the like, for example. It is to be noted that the calculation unit 30 may obtain the information to be used of the skeleton component B from the extraction unit 10 or from the memory 20.

The calculation unit 30 calculates the attenuation factor based on the following calculation method, for example. The calculation method described here is a calculation method based on the following statistical knowledge. The knowledge is that, in the captured image (input image) of the real scene with the imaging device 7, the color channel in which the reflected light is zero or extremely low exists in at least one pixel in a local image region, as illustrated in FIG. 3.

The calculation unit 30 calculates the attenuation factor at(p) of the reflected light based on the formula (3).

$$at(p) = r \times \min_{\forall \lambda}(B(p,\lambda)) \quad (3)$$

More specifically, the calculation unit 30 calculates the attenuation factor at(p) of the reflected light by multiplying a minimum value ($\min_{\forall \lambda}(B(p, \lambda))$) of the skeleton components B of all color channels to be analyzed in the pixel at the coordinate position p in the skeleton image by a ratio r. The attenuation factor at(p) is a value larger than 0 and smaller than 1 (0<at(p)<1). In addition, the ratio r is a constant given in advance, and is approximately 0.7 to 0.8, for example. It is to be noted that the ratio r is not limited to approximately 0.7 to 0.8. In addition, the minimum value ($\min_{\forall \lambda}(B(p, \lambda))$) may be a value that takes not only the pixel at the coordinate position p but also the skeleton components B in a plurality of pixels existing around the pixel into consideration.

The calculation unit 30 has a function to calculate attenuation factors for all pixels in the skeleton image and generate an attenuation factor image based on the calculated attenuation factors. The attenuation factor image is an image in which the pixel value of the pixel at the coordinate position p is a value calculated based on the attenuation factor at(p).

Figure 4:
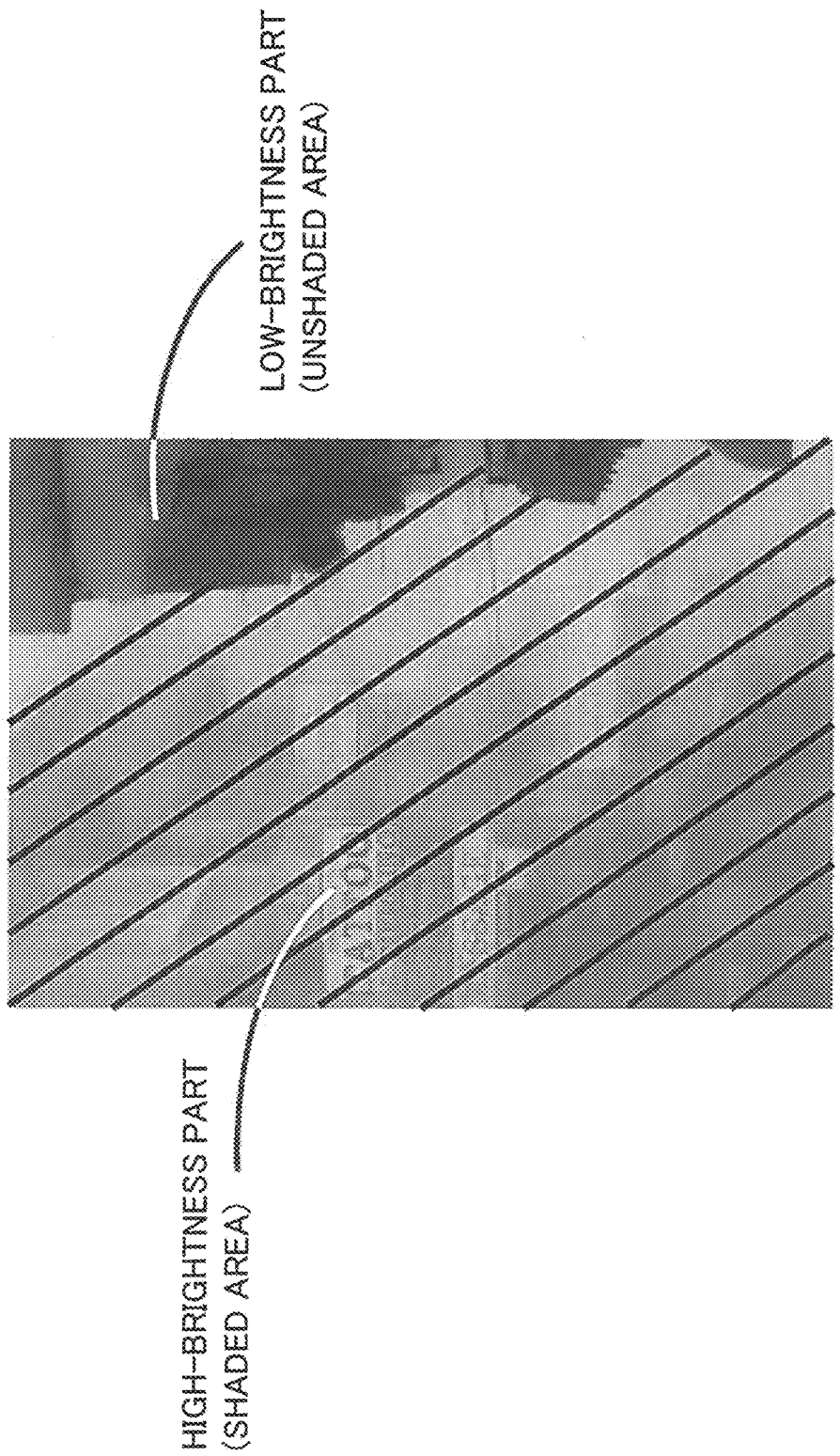
FIG. 4 is a diagram illustrating an example of an attenuation factor image in the first exemplary embodiment.

FIG. 4 is an example of the attenuation factor image generated by the calculation unit 30. A shaded area of the attenuation factor image illustrated in FIG. 4 is a high-brightness (bright) image part. The high-brightness (bright) image part represents that the attenuation factor of the reflected light from an object is high. This is because a lot of scattered components of the environment light are included due to the influence of smoke. In addition, an unshaded area of the attenuation factor image illustrated in FIG. 4 is a low-brightness (dark) image part. The low-brightness (dark) image part represents that the attenuation factor of the reflected light from the object is low because of being uninfluenced by smoke. More specifically, the attenuation factor image is an image in which the attenuation factor in each of the pixels is represented as the brightness of the pixel.

The detection unit 40 has a function to detect generation of smoke by analyzing the brightness of the attenuation factor image by the calculation unit 30 and determining whether smoke appears (is generated) in the scene. As described above, the attenuation factor image is the image in which the attenuation factor in each of the pixels is represented as the brightness of the pixel. When smoke is generated in the scene that appears in the captured image, the attenuation factor of the reflected light in the captured image becomes high, and thus, the attenuation factor image has high brightness. Accordingly, when the attenuation factor image is wholly bright, the attenuation factor image represents a situation where the whole of the scene that appears in the captured image is filled with smoke. In addition, when a partial region in the attenuation factor image is bright, the attenuation factor image represents a situation where smoke is generated in the bright region.

The detection unit 40 detects generation of smoke in the following manner, for example. More specifically, the attenuation factor image based on the captured image (input image) obtained by imaging a scene to be monitored under a situation where smoke is not generated with the imaging device 7 has been provided to the detection device 100 as a reference attenuation factor image. The detection unit 40 compares the reference attenuation factor image with the attenuation factor image by the calculation unit 30. The detection unit 40 determines whether smoke is generated in the scene to be monitored by the comparison result.

For example, a brightness difference between the reference attenuation factor image and the attenuation factor image by the calculation unit 30 is used for the determination. In other words, the detection unit 40 determines whether the brightness difference between the brightness of each of the pixels in the whole or partial region of the attenuation factor image by the calculation unit 30 and the brightness of a pixel of the reference attenuation factor image, which corresponds to the pixel, exceeds a predetermined first threshold value. Then, the detection unit 40 counts the number of pixels whose brightness differences exceed the first threshold value based on the comparison result, and determines that smoke is generated in the scene to be monitored when the number of the pixels exceeds a predetermined second threshold value. It is to be noted that, for example, when counting the number of pixels whose brightness differences exceed the first threshold value, if a pixel whose brightness difference exceeds the first threshold value is an isolated point, the detection unit 40 does not count the pixel.

The detection unit 40 outputs the determination result of whether smoke is generated. For example, when smoke is generated, the detection unit 40 outputs, as information of the determination result, an alarm signal that reports that smoke is generated and an image representing the situation where smoke is generated (for example, one or both of the input image and the attenuation factor image). It is to be noted that the detection unit 40 may output an edited image in which a part in which smoke is generated is emphasized with a frame border (at least one of the input image and the attenuation factor image), for example. In addition, the detection unit 40 may extract an image part in which smoke is generated from the input image to output the image part, for example.

In addition, when determining that smoke is not generated, the detection unit 40 outputs a signal that reports that smoke is not generated, or may report that smoke is not generated by not outputting a signal.

Furthermore, the detection unit 40 may have a function, when determining that smoke is generated, to estimate concentration of the smoke that appears in the input image (captured image) using information of the attenuation factor, for example.

It is to be noted that the detection unit 40 may determine whether smoke is generated in each of segmented regions of the attenuation factor image segmented into multiple regions. For example, the detection unit 40 calculates the brightness difference between the reference attenuation factor image and the attenuation factor image by the calculation unit 30 for each of the pixels in the similar way to the above. Then, the detection unit 40 calculates a total value of the brightness difference for each of the segmented regions of the attenuation factor image, and determines that smoke is generated in a scene part corresponding to a segmented region having the calculated value equal to or more than a predetermined third threshold value. By determining whether smoke is generated for each of the segmented regions of the attenuation factor image, the detection unit 40 can provide information representing that smoke is generated in a partial region of the scene to be monitored or the whole of the scene to be monitored is filled with smoke It is to be noted that, in the above-described example, the reference attenuation factor image is an image based on a scene of a situation where smoke is not generated. In place of this, the reference attenuation factor image may be an attenuation factor image based on a scene of a situation where haze due to small fire that is an initial state of fire (smoke generated in the early phase of fire) is generated, for example.

Figure 5:
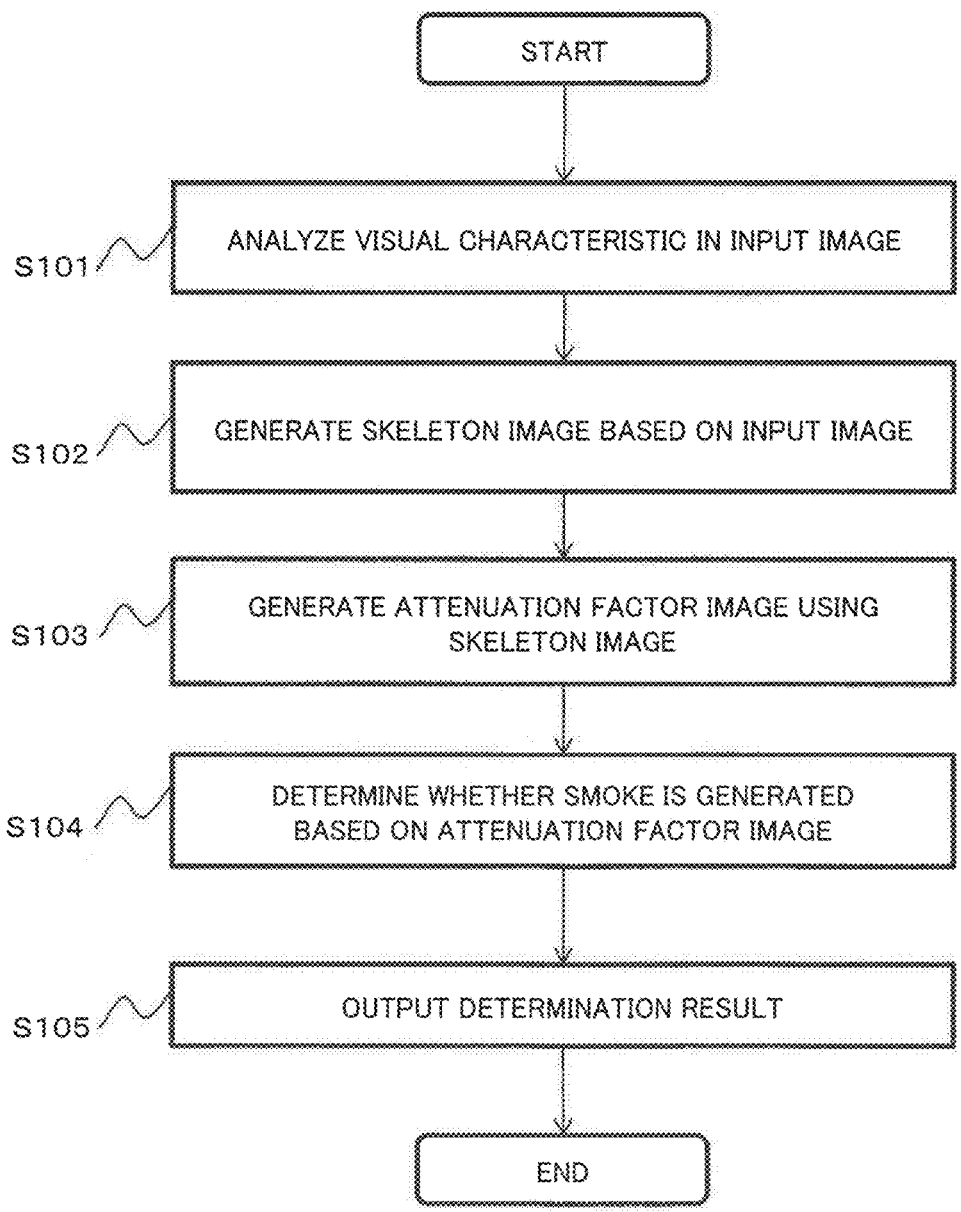
FIG. 5 is a flow chart illustrating an operation example of the detection device of the first exemplary embodiment.

Hereinafter, an example of the operation of the detection device 100 in the first exemplary embodiment will be described using FIG. 5. It is to be noted that FIG. 5 is a flow chart illustrating an example of the operation of the detection device 100, and a processing procedure that the detection device 100 executes is illustrated. The processing procedure illustrated here is merely an example, and the processing procedure may be changed or the processing may be repeated, appropriately.

For example, when receiving an input image obtained by capturing a real scene (scene to be monitored), the extraction unit 10 analyzes the visual characteristic in the input image (S101). Then, the extraction unit 10 extracts the skeleton component from the input image using the analysis result, and generates the skeleton image (S102). The extraction unit 10 stores information of the skeleton image in the memory 20.

After that, the calculation unit 30 calculates the attenuation factors for all pixels of the generated skeleton image, and generates the attenuation factor image (S103). Then, the detection unit 40 determines whether smoke is generated in the scene to be monitored based on the brightness of each of the pixels in the attenuation factor image (S104). After that, the detection unit 40 outputs the determination result (S105).

The detection device 100 in the first exemplary embodiment generates the skeleton image by analyzing the input image (the captured image of scene to be monitored), calculates the attenuation factors in all pixels of the skeleton image, and generates the attenuation factor image based on the attenuation factors. Then, the detection device 100 detects (determines) generation of smoke in the scene to be monitored by analyzing the brightness of the attenuation factor image. The detection device 100 has the foregoing functions, and thus, can achieve stable and high-accuracy smoke detection with no influence of noise of the image, and color and intensity of environment light in the scene to be monitored. In other words, the detection device 100 uses the skeleton image based on the skeleton component without noise in the image when detecting smoke, and thus, can suppress a decrease in performance of smoke detection due to the noise of the image.

In addition, the detection device 100 can detect small fire (haze) that is the initial state of fire by determining whether smoke is generated in the scene to be monitored using the brightness of the attenuation factor image based on the skeleton image. Therefore, the detection device 100 can issue the alarm at the stage of small fire, and thus, can contribute to prevention of fire spreading.

Second Exemplary Embodiment

Hereinafter, a second exemplary embodiment according to the present invention will be described. It is to be noted that, in the description of the second exemplary embodiment, the same components as the components in the detection device of the first exemplary embodiment are denoted by the same reference signs, and the overlapping description of the common matter will be omitted.

Figure 6:
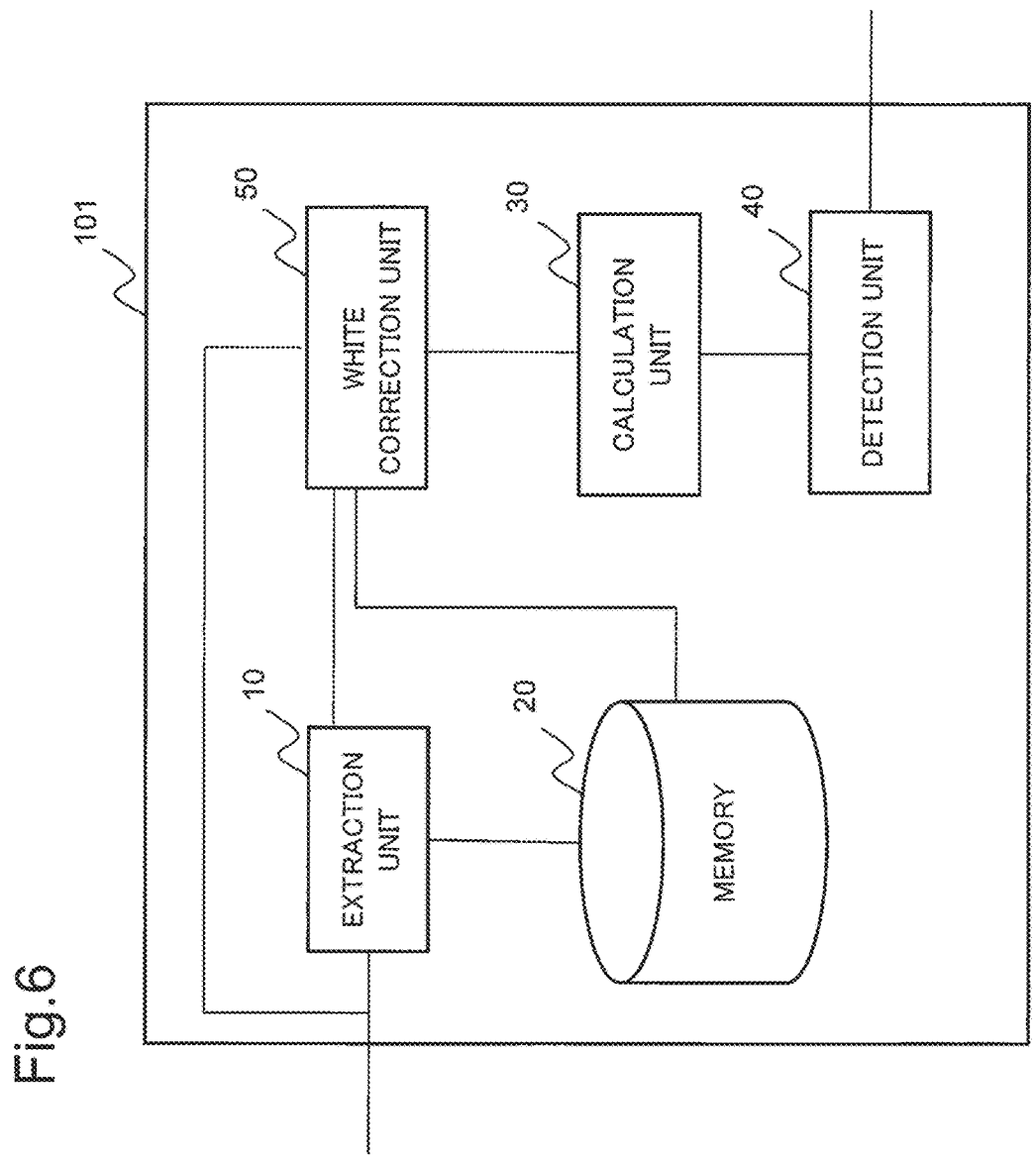
FIG. 6 is a block diagram simply illustrating a configuration of a detection device of a second exemplary embodiment according to the present invention.

FIG. 6 is a block diagram illustrating a functional configuration of a detection device 101 in the second exemplary embodiment. The detection device 101 includes a white correction unit 50 in addition to the extraction unit 10, the memory 20, the calculation unit 30, and the detection unit 40 described in the first exemplary embodiment. Since the respective functions of the extraction unit 10, the memory 20, the calculation unit 30, and the detection unit 40 are the same as the functions described in the first exemplary embodiment, the overlapping description of the common matter will be omitted here.

Figure 7:
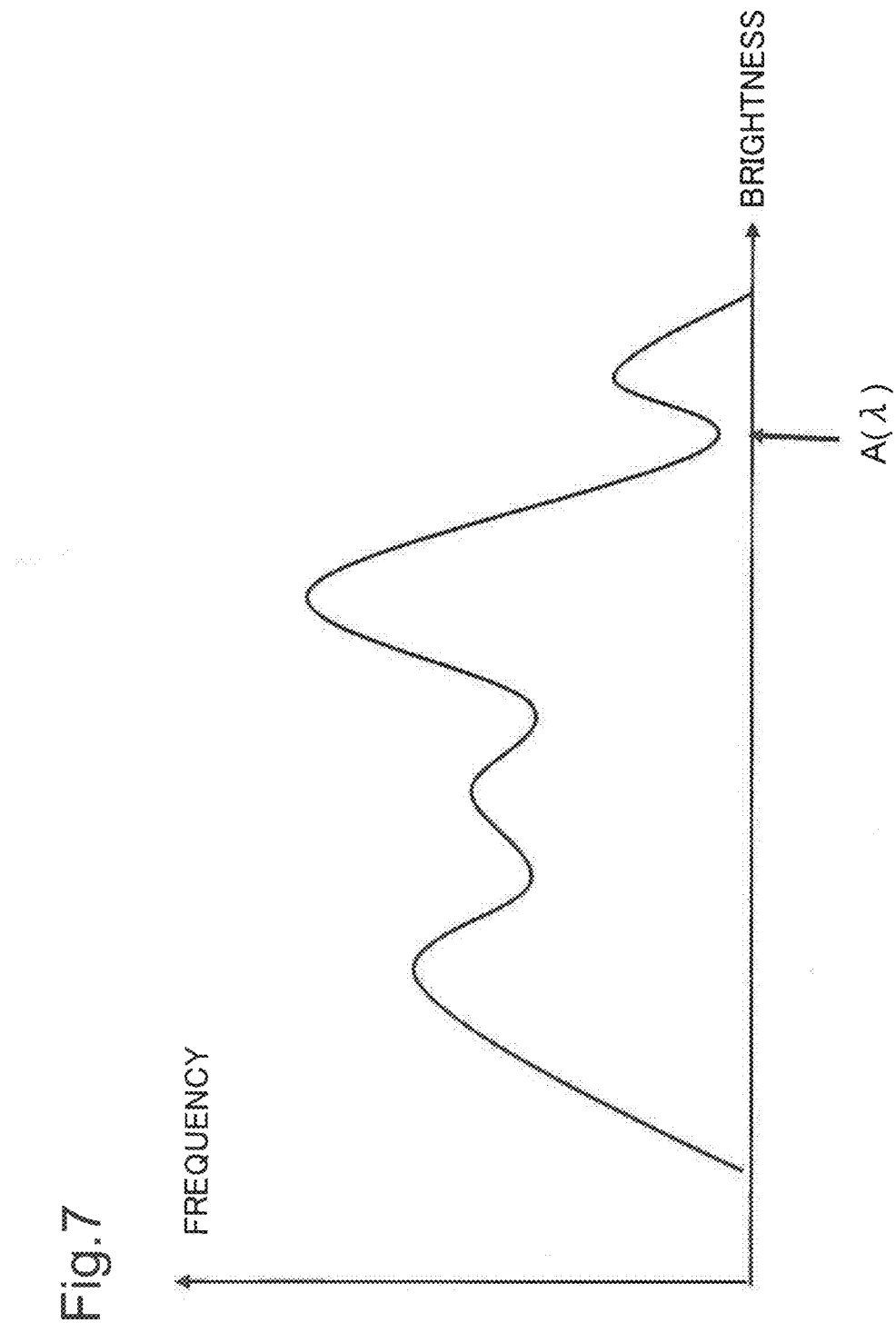
FIG. 7 is a graph illustrating an example of a histogram used when calculating environment light.

The white correction unit 50 has a function to calculate a color $A(\lambda)$ of the environment light in the scene to be monitored based on the color information and the brightness information included in the input image or the skeleton image. For example, with respect to the input image or the skeleton image, the white correction unit 50 generates a histogram as illustrated in FIG. 7 for each color channel. The horizontal axis and the vertical axis of the graph illustrated in FIG. 7 show the brightness of the color channel and the frequency (number of pixels), respectively. The histogram illustrated in FIG. 7 is a graph showing a relationship between the brightness in each color channel and the number of the pixels (frequency) having the brightness of the color channel in the input image or the skeleton image.

After generating the histogram, the white correction unit 50 adds up the number of the pixels (frequency) from the high-brightness (bright) side in the histogram for each color channel. Then, the white correction unit 50 calculates the brightness at a brightness position where the accumulated value of the addition reaches a predetermined value G as the color $A(\lambda)$ of the environment light. In other words, for each color channel, the white correction unit 50 calculates the color $A(\lambda)$ of the environment light by removing information of an overexposed image part by the above-described method. It is to be noted that, instead of directly using the brightness at the brightness position where the accumulated value reaches the value G as the color $A(\lambda)$ of the environment light, the white correction unit 50 may use a calculated value obtained by further multiplying the brightness at the brightness position by a predetermined ratio as the color $A(\lambda)$ of the environment light. In addition, a limit value is set, and when the accumulated value reaches the limit value before reaching the value G, the white correction unit 50 may calculate the brightness at the brightness position as the color $A(\lambda)$ of the environment light.

The white correction unit 50 further has a function to correct the skeleton image B generated by the extraction unit 10 using the calculated color $A(\lambda)$ of the environment light. For example, the white correction unit 50 has a function to calculate (generate) the skeleton image $B1(p, \lambda)$ after correction, normalized by the color $A(\lambda)$ of the environment light based on the formula (4). It is to be noted that, since the information of the skeleton image is a set of the skeleton components $B(p, \lambda)$, the skeleton image generated by the extraction unit 10 is also referred to as $B(p, \lambda)$, and furthermore, the skeleton image after correction by the white correction unit 50 is referred to as $B1(p, \lambda)$ here.

$$B1(p, \lambda) = \frac{\max_{\forall \lambda} A(\lambda)}{A(\lambda)} \times B(p, \lambda) \quad (4)$$

In the second exemplary embodiment, the calculation unit 30 calculates the attenuation factor of the reflected light using the skeleton image after correction by the white correction unit 50 without using the skeleton image generated by the extraction unit 10.

The detection device 101 of the second exemplary embodiment includes the white correction unit 50 in addition to the configuration described in the first exemplary embodiment. Thus, the detection device 101 can more improve the detection accuracy of generation of smoke. More specifically, the captured image (input image) and the skeleton image obtained from the input image are not necessarily white balanced or color balanced. The calculation unit 30 sometimes cannot calculate the accurate attenuation factor under a situation where white balance or color balance of the captured image (input image) and the skeleton image is disrupted. In contrast, in the second exemplary embodiment, the white correction unit 50 corrects (adjusts) the white balance or the color balance of the skeleton image by normalizing the skeleton image by the environment light. Therefore, the detection device 101 improves the accuracy of the attenuation factor by the calculation unit 30, and thus, can more improve the detection accuracy of generation of smoke.

Third Exemplary Embodiment

Hereinafter, a third exemplary embodiment according to the present invention will be described. It is to be noted that, in the description of the third exemplary embodiment, the same components as the components that configure the detection devices of the first exemplary embodiment and the second exemplary embodiment are denoted by the same reference signs, and the overlapping description of the common matter will be omitted.

Figure 8:
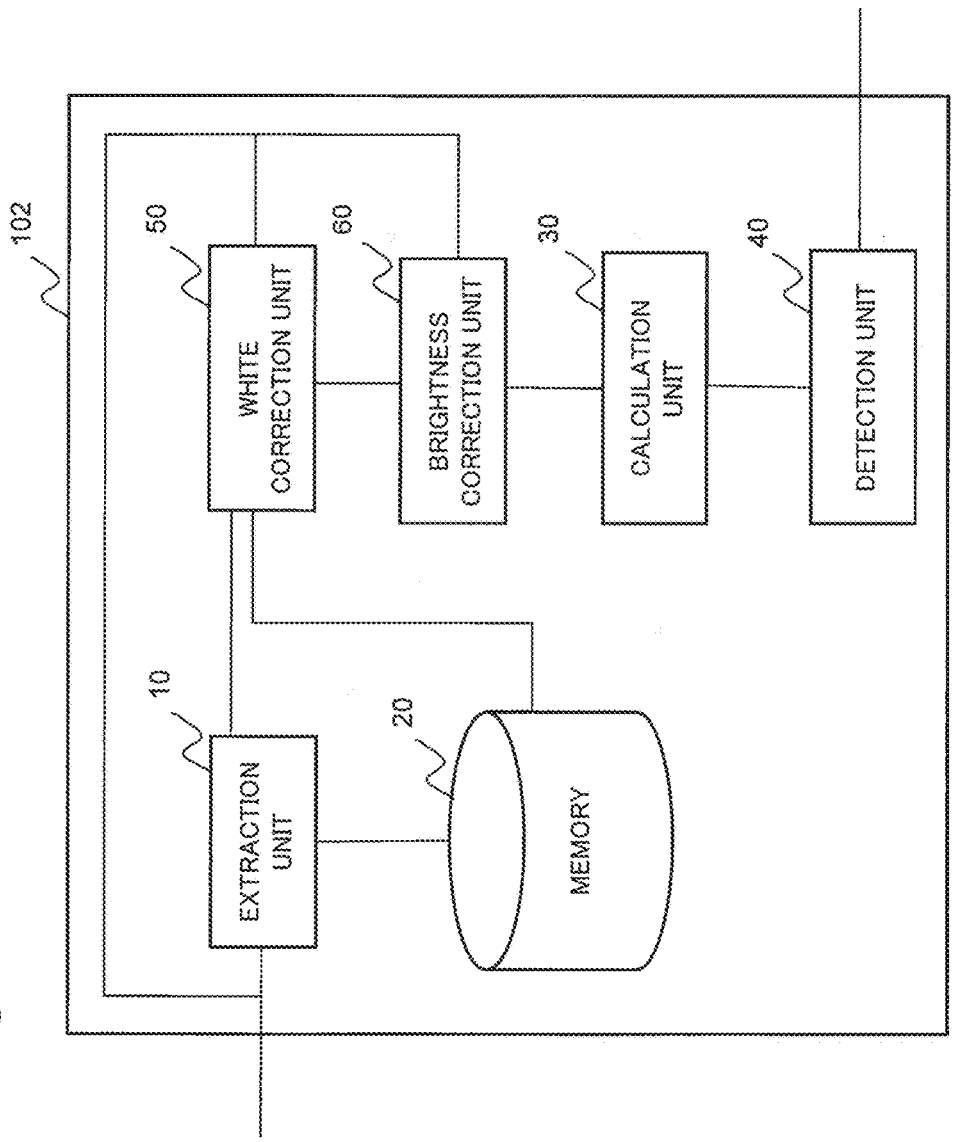
FIG. 8 is a block diagram simply illustrating a configuration of a detection device of a third exemplary embodiment according to the present invention.

FIG. 8 is a block diagram simply illustrating a functional configuration of a detection device of a third exemplary embodiment. A detection device 102 of the third exemplary embodiment includes a brightness correction unit 60 in addition to the functional configuration of the second exemplary embodiment. It is to be noted that, since the configurations (functions) of the extraction unit 10, the memory 20, the calculation unit 30, the detection unit 40, and the white correction unit 50 are described above, the overlapping description of the common matter will be omitted here.

The brightness correction unit 60 has a function to correct the brightness of the skeleton image. For example, the brightness correction unit 60 generates the histogram as in FIG. 7 in the input image or the skeleton image B1 after correction based on the brightness information included in the input image or the skeleton image B1 after correction by the white correction unit 50. Then, the brightness correction unit 60 evaluates average brightness of the whole image based on the histogram. Furthermore, the brightness correction unit 60 calculates a gamma correction parameter γ that corrects the evaluated average brightness to be target brightness. The gamma correction parameter γ is calculated using the formula (5), for example.

$$\gamma = \ln(q) \div \ln(p) \quad (5)$$

It is to be noted that, in the formula (5), q represents the target brightness. As the target brightness, for example, an average value or a median value of the brightness of the whole captured image obtained by capturing the scene to be monitored under a situation where smoke is not generated is set. p represents the average brightness in the skeleton image B1 whose brightness is to be corrected. ln represents a logarithmic function.

The brightness correction unit 60 corrects the brightness of the skeleton image B1 to generate the skeleton image B2 after brightness correction using the calculated gamma correction parameter γ and the formula (6).

$$B2(p,\lambda) = (B1(p,\lambda))^\gamma \quad (6)$$

The detection device 102 of the third exemplary embodiment includes the brightness correction unit 60 in addition to the configuration described in the second exemplary embodiment. Thus, the detection device 102 can more improve the detection accuracy of generation of smoke. More specifically, when the detection unit 40 compares the attenuation factor image by the calculation unit 30 with the reference attenuation factor image, if the average brightness of the attenuation factor image and the average brightness of the reference attenuation factor image are extremely different, the accurate comparison result cannot be obtained, and the detection accuracy of generation of smoke may be reduced. In contrast, in the third exemplary embodiment, the detection device 102 can match the average brightness of the reference attenuation factor image with the average brightness of the attenuation factor image using the brightness correction unit 60. Therefore, the detection device 102 can determine whether smoke is generated without harmful influence of the brightness change of the attenuation factor image by the calculation unit 30, and thus, can detect that smoke is generated stably and with high accuracy.

Figure 9:
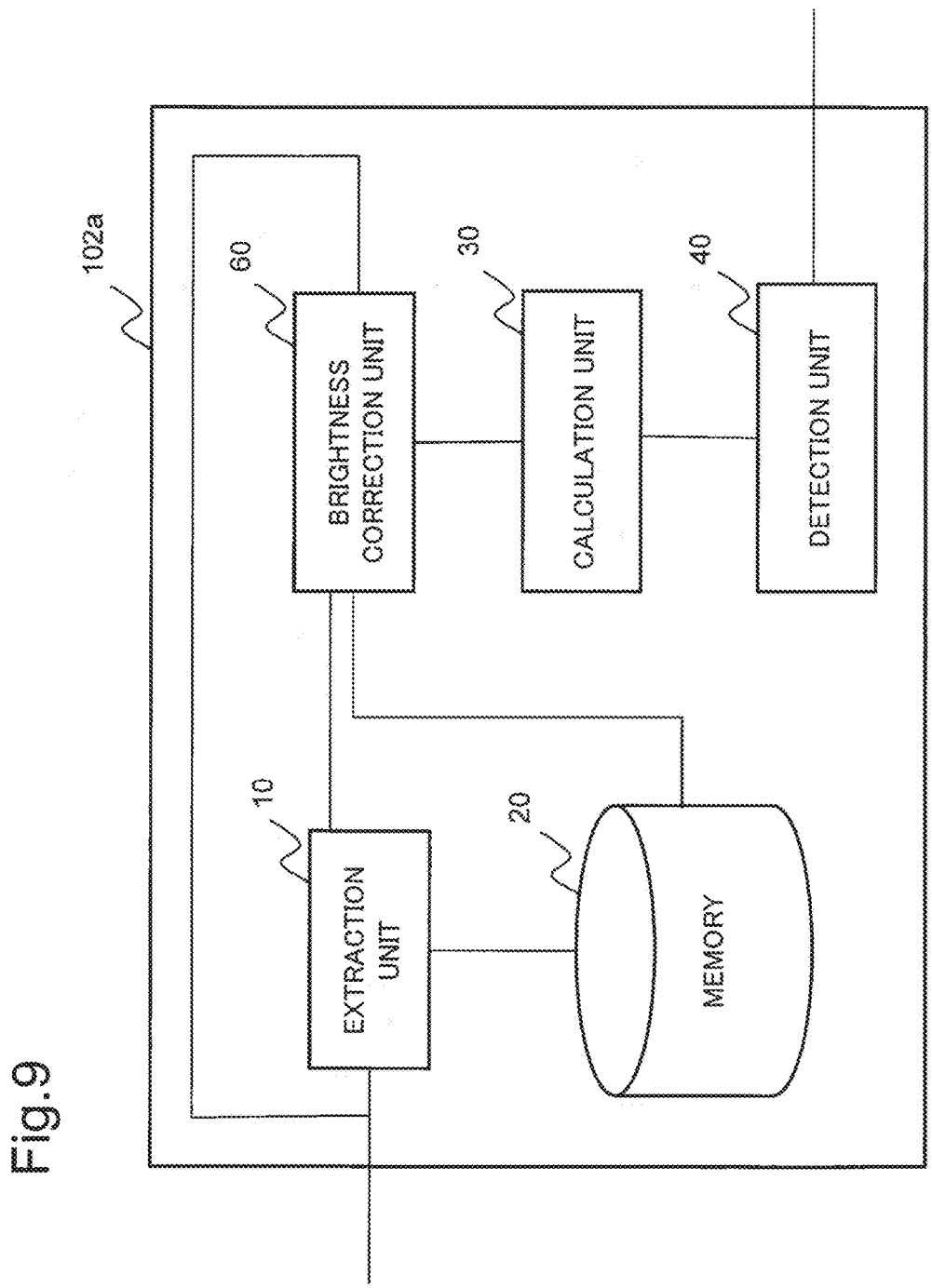
FIG. 9 is a block diagram for explaining a modified example of the third exemplary embodiment according to the present invention.

It is to be noted that, although the detection device 102 of the third exemplary embodiment has the white correction unit 50, as illustrated in FIG. 9, a detection device 102a may include a configuration without the white correction unit 50. In this case, the brightness correction unit 60 corrects the brightness of not the skeleton image B1 after correction by the white correction unit 50 but the skeleton image B generated by the extraction unit 10.

Fourth Exemplary Embodiment

Hereinafter, a fourth exemplary embodiment according to the present invention will be described. It is to be noted that, in the description of the fourth exemplary embodiment, the same components as the components that configure the detection devices of the above-described respective exemplary embodiments are denoted by the same reference signs, and the overlapping description of the common matter will be omitted.

Figure 10:
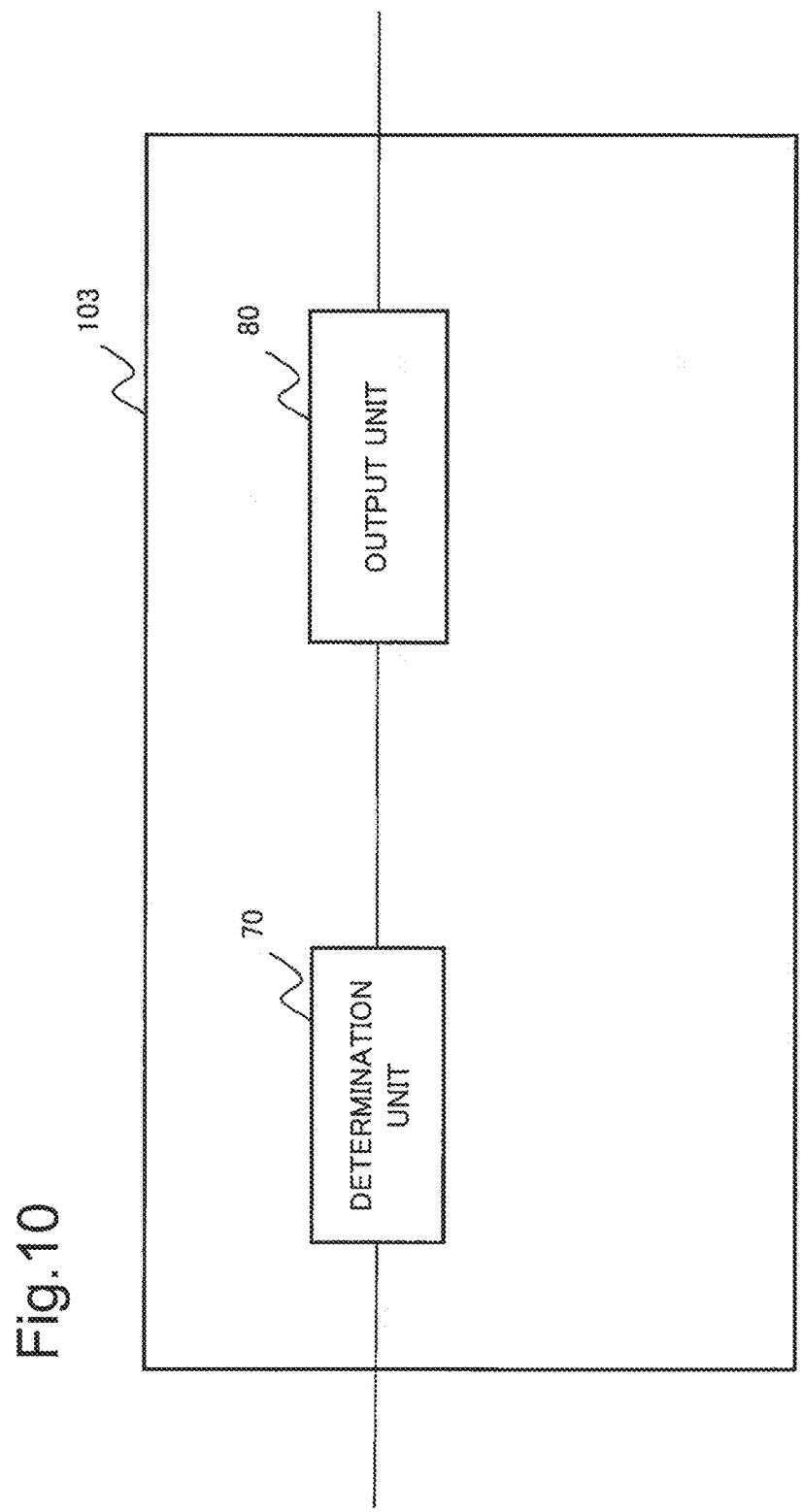
FIG. 10 is a block diagram simply illustrating a configuration of a detection device of a fourth exemplary embodiment according to the present invention.

FIG. 10 simply illustrates a functional configuration of a detection device 103 of the fourth exemplary embodiment. The detection device 103 of the fourth exemplary embodiment includes a determination unit 70 and an output unit 80. The determination unit 70 has a function to determine whether smoke is captured in an inputted image. The output unit 80 has a function, when smoke is captured in the inputted image, to output a notification reporting that the smoke has been detected. It is to be noted that the respective functions of the determination unit 70 and the output unit 80 are achieved by the configurations of the above-described respective exemplary embodiments, for example.

The detection device 103 of the fourth exemplary embodiment can also appropriately detect that smoke is generated by the captured image (input image) obtained by capturing the scene to be monitored and an image analysis of the image.

Fifth Exemplary Embodiment

Hereinafter, a fifth exemplary embodiment according to the present invention will be described. It is to be noted that, in the description of the fifth exemplary embodiment, the same components as the components that configure the detection device 103 of the fourth exemplary embodiment are denoted by the same reference signs, and the overlapping description of the common matter will be omitted.

Figure 11:
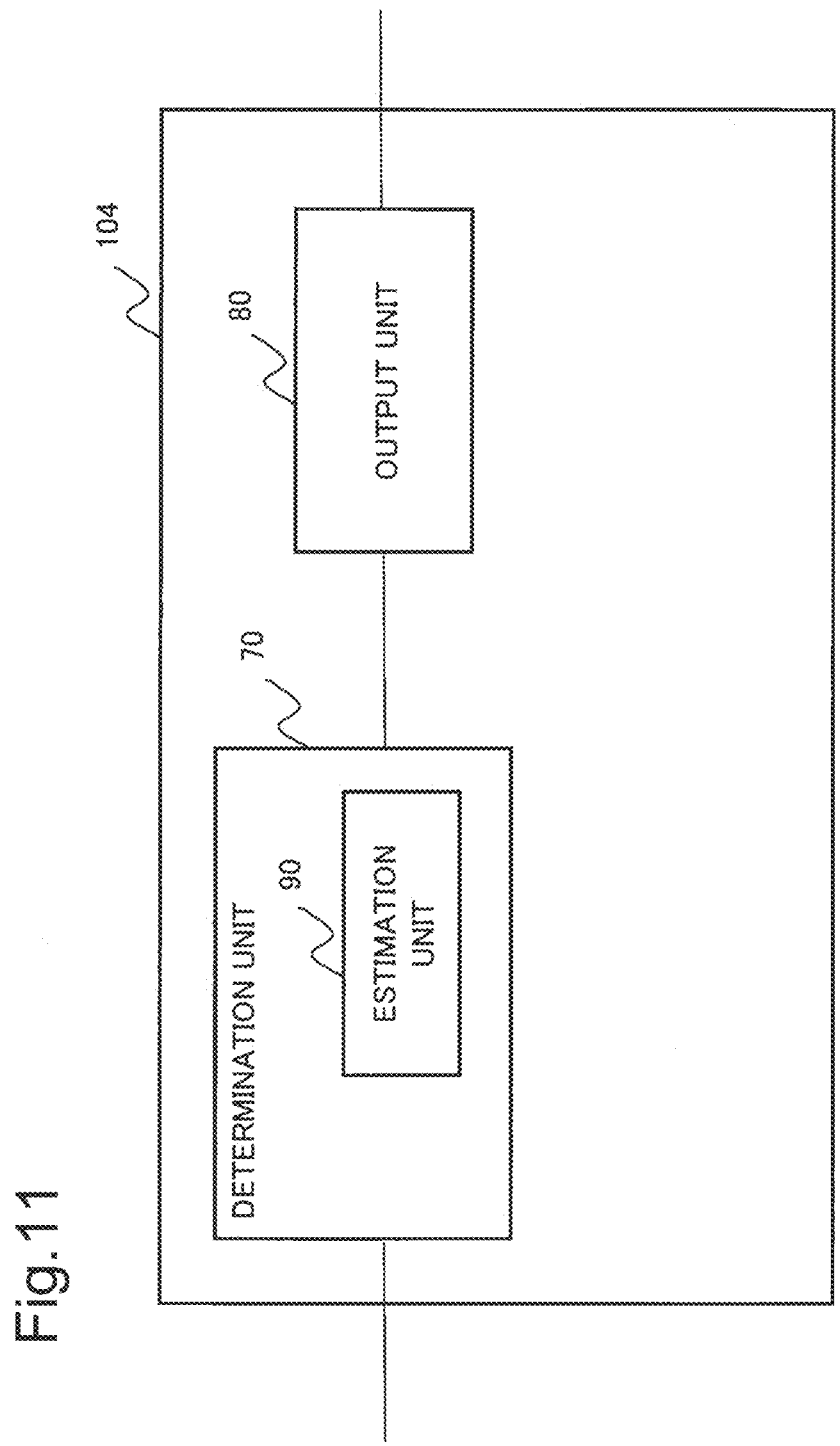
FIG. 11 is a block diagram simply illustrating a configuration of a detection device of a fifth exemplary embodiment according to the present invention.

FIG. 11 is a block diagram simply illustrating a functional configuration of a detection device 104 of the fifth exemplary embodiment. The detection device 104 of the fifth exemplary embodiment includes the determination unit 70 and the output unit 80, and the determination unit 70 includes an estimation unit 90.

The estimation unit 90 has a function, when smoke is captured in the input image, to estimate the concentration of the smoke by the image analysis. The output unit 80 has a function, when smoke is captured in the input image, to not only output the notification reporting that the smoke has been detected but also output information reporting the concentration of the smoke estimated by the estimation unit 90.

The detection device 104 of the fifth exemplary embodiment includes the same configuration as the detection device 103 of the fourth exemplary embodiment, and thus, can appropriately detect that smoke is generated in the scene to be monitored as is the case with the fourth exemplary embodiment. Furthermore, the detection device 104 also outputs the information of the concentration of the detected smoke, and therefore, can provide a criterion to determine that the source of the smoke is small fire or spreading fire, for example.

Heretofore, the invention of the present application has been described using the exemplary embodiments, but the invention of the present application is not necessarily limited to the above-described exemplary embodiments. With respect to the configuration and details of the invention of the present application, various changes can be made and implemented within the range of the technical idea thereof which those skilled in the art can understand within the scope of the invention of the present application.

For example, the attenuation factor image in each of the first to third exemplary embodiments is the image in which the pixel value of the pixel at the coordinate position p is a value calculated based on the attenuation factor at(p). In contrast, the attenuation factor image may be an image in which the pixel value of the pixel at the coordinate position p is the attenuation factor at(p) itself. It is to be noted that the attenuation factor image by the attenuation factor at(p) is also referred to as the attenuation factor image at(p).

Since the attenuation factor of the reflected light is information that varies in accordance with a generation situation of smoke, even if the attenuation factor image by the calculation unit 30 is the attenuation factor image at(p), the detection unit 40 can perform smoke detection by executing the same processing as above.

This application claims priority based on Japanese Patent Application No. 2014-067596 filed on Mar. 28, 2014, the disclosure of which is incorporated herein in its entirety.

A part or all of the above-described exemplary embodiments can also be described as the following supplementary notes, but are not limited thereto.

[Supplementary Note 1]

A detection device includes:

a determination unit that determines whether a sign of smoke is captured in an image of an input image of being an inputted image; and an output unit that outputs a notification reporting that the sign of smoke is captured in the image.

[Supplementary Note 2]

In the detection device according to supplementary note 1, the determination unit includes an estimation unit that estimates a concentration of the smoke in the image, and the output unit outputs information on the concentration of the smoke.

[Supplementary Note 3]

In the detection device according to supplementary note 1 or 2, the determination unit includes:

a skeleton image extraction unit that extracts a skeleton component representing a comprehensive image structure from the input image, and generates a skeleton image in accordance with the skeleton component;

an attenuation factor calculation unit that calculates an attenuation factor of light from the skeleton image in a local region in a scene, and generates an attenuation factor image of the input image in accordance with the attenuation factor; and a smoke generation detection unit that determines whether the sign of smoke is captured in the image by comparing the attenuation factor image with a reference attenuation factor image generated in accordance with an attenuation factor of light under a situation where the sign of smoke is not generated.

[Supplementary Note 4]

The detection device according to supplementary note 3 includes a white correction unit that calculates a color of environment light in the scene from the input image or the skeleton image, and corrects a white color of the skeleton image based on the color of environment light.

[Supplementary Note 5]

The detection device according to supplementary note 3 or 4 includes:

a brightness correction unit that evaluates average brightness of the input image or the skeleton image, and corrects the skeleton image such that the average brightness is predetermined brightness.

[Supplementary Note 6]

The detection device according to supplementary note 3 includes:

a white correction unit that calculates a color of environment light in the scene from the input image or the skeleton image, and corrects a white color of the skeleton image based on the color of environment light; and a brightness correction unit that evaluates average brightness of the input image or the skeleton image whose white color has been corrected, and corrects the skeleton image whose white color has been corrected such that the average brightness is target brightness.

[Supplementary Note 7]

A detection method includes:

determining whether a sign of smoke is captured in an image of an input image that is an inputted image; and outputting a notification reporting that the sign of smoke is captured in the image.

[Supplementary Note 8]

The detection method according to supplementary note 7 includes:

estimating a concentration of the smoke in the image; and outputting information on the concentration of the smoke.

[Supplementary Note 9]

The detection method according to supplementary note 7 or 8 includes:

in the step of determining whether the sign of smoke is captured in the image, extracting a skeleton component representing a comprehensive image structure from the input image, and generating a skeleton image in accordance with the skeleton component;

calculating an attenuation factor of light from the skeleton image in a local region in a scene, and generating an attenuation factor image of the input image in accordance with the attenuation factor; and determining whether the sign of smoke is captured in the image by comparing the attenuation factor image with a reference attenuation factor image generated in accordance with an attenuation factor of light under a situation where the sign of smoke is not generated.

[Supplementary Note 10]

The detection method according to supplementary note 9 includes:

calculating a color of environment light in the scene from the input image or the skeleton image, and correcting a white color of the skeleton image based on the color of environment light.

[Supplementary Note 11]

The detection method according to supplementary note 9 or 10 includes:

evaluating average brightness of the input image or the skeleton image, and correcting the skeleton image such that the average brightness is predetermined brightness.

[Supplementary Note 12]

The detection method according to supplementary note 9 includes:

calculating a color of environment light in the scene from the input image or the skeleton image, and correcting a white color of the skeleton image based on the color of environment light; and evaluating average brightness of the input image or the skeleton image whose white color has been corrected, and correcting the skeleton image whose white color has been corrected such that the average brightness is target brightness.

[Supplementary Note 13]

A program makes a computer execute:

determining whether a sign of smoke is captured in an image of an input image that is an inputted image; and outputting a notification representing that the sign of smoke is captured in the image.

[Supplementary Note 14]

The program according to supplementary note 13 makes the computer execute:

estimating a concentration of the smoke in the image; and outputting information on the concentration of the smoke.

[Supplementary Note 15]

The program according to supplementary note 13 or 14 includes:

in the determining whether the sign of smoke is captured in the image, extracting a skeleton component representing a comprehensive image structure from the input image, and generating a skeleton image in accordance with the skeleton component;

calculating an attenuation factor of light from the skeleton image in a local region in a scene, and generating an attenuation factor image of the input image in accordance with the attenuation factor; and determining whether the sign of smoke is captured in the image by comparing the attenuation factor image with a reference attenuation factor image generated in accordance with an attenuation factor of light under a situation where the sign of smoke is not generated.

[Supplementary Note 16]

The program according to supplementary note 15 makes the computer execute:

calculating a color of environment light in the scene from the input image or the skeleton image, and correcting a white color of the skeleton image based on the color of environment light.

[Supplementary Note 17]

The program according to supplementary note 15 or 16 makes the computer execute:

evaluating average brightness of the input image or the skeleton image, and correcting the skeleton image such that the average brightness is predetermined brightness.

[Supplementary Note 18]

The program according to supplementary note 15 makes the computer execute:

calculating a color of environment light in the scene from the input image or the skeleton image, and correcting a white color of the skeleton image based on the color of environment light; and evaluating average brightness of the input image or the skeleton image whose white color has been corrected, and correcting the skeleton image whose white color has been corrected such that the average brightness is target brightness.

[Supplementary Note 19]

A detection device includes:

a skeleton image extraction unit that extracts a skeleton component representing a comprehensive image structure from an input image, and generates a skeleton image;

a white correction unit that calculates a color of environment light in a scene from the input image or the skeleton image, and corrects a white color of the skeleton image based on the color of environment light;

a brightness correction unit that evaluates average brightness of the input image or the skeleton image whose white color has been corrected, and corrects the skeleton image whose white color has been corrected such that the average brightness is target brightness;

an attenuation factor calculation unit that calculates an attenuation factor of light from the skeleton image whose brightness has been corrected based on statistical knowledge that a color channel whose brightness is low exists in a local region in the scene, and generates an attenuation factor image; and a smoke generation detection unit that determines the presence or absence of generation of smoke by comparing the attenuation factor image with a reference attenuation factor image under a situation where smoke is not generated.

[Supplementary Note 20]

A smoke generation detection method includes:

extracting a skeleton component representing a comprehensive image structure from an input image, and generating a skeleton image;

calculating a color of environment light in a scene from the input image or the skeleton image, and correcting a white color of the skeleton image based on the color of environment light;

evaluating average brightness of the input image or the skeleton image whose white color has been corrected, and correcting the skeleton image whose white color has been corrected such that the average brightness is target brightness;

calculating an attenuation factor of light from the skeleton image whose brightness has been corrected based on statistical knowledge that a color channel whose brightness is low exists in a local region in the scene, and generating an attenuation factor image; and determining the presence or absence of generation of smoke by comparing the attenuation factor image with a reference attenuation factor image under a situation where smoke is not generated.

[Supplementary Note 21]

A program makes a computer execute:

extracting a skeleton component representing a comprehensive image structure from an input image, and generating a skeleton image;

calculating a color of environment light in a scene from the input image or the skeleton image, and correcting a white color of the skeleton image based on the color of environment light;

evaluating average brightness of the input image or the skeleton image whose white color has been corrected, and correcting the skeleton image whose white color has been corrected such that the average brightness is target brightness;

calculating an attenuation factor of light from the skeleton image whose brightness has been corrected based on statistical knowledge that a color channel whose brightness is low exists in a local region in the scene, and generating an attenuation factor image; and determining the presence or absence of generation of smoke by comparing the attenuation factor image with a reference attenuation factor image under a situation where smoke is not generated.

REFERENCE SIGNS LIST 10 extraction unit
20 memory
30 calculation unit
40 detection unit
50 white correction unit
60 brightness correction unit
70 determination unit
80 output unit
90 estimation unit
100, 101, 102, 102a, 103, 104 detection device

What is claimed is:

1. A detection device comprising:
a processor that is configured to:
by using a result of an image analysis of an input image that is a captured image obtained by capturing a scene to be monitored, generate a noise removal image obtained by removing a noise component from the input image;
by using brightness information included in the noise removal image generated, calculate an attenuation factor of reflected light from an object captured in the input image for each pixel of the input image;
generate an attenuation factor image in which the attenuation factor in each pixel is represented as brightness of the pixel; and
determine whether smoke is generated in the scene to be monitored based on a brightness difference between a reference attenuation factor image and the attenuation factor image, the reference attenuation factor image being an image in which the attenuation factor, which is obtained from an image captured under a situation where smoke is not generated, is represented as brightness of the pixel in each pixel.

2. The detection device according to claim 1, wherein the processor further adjusts color balance of the noise removal image.

3. The detection device according to claim 2, wherein
the processor calculates a color of environment light in the scene to be monitored based on color information and the brightness information included in the input image or the noise removal image, and adjusts the color balance of the image using information of the calculated color of environment light.

4. The detection device according to claim 1,
wherein the processor further adjusts brightness of the noise removal image.

5. The detection device according to claim 4, wherein
the processor calculates average brightness of the input image or the noise removal image based on the brightness information included in the input image or the noise removal image, and adjusts the brightness of the noise removal image to be target brightness using the average brightness.

6. The detection device according to claim 1, wherein
the processor extracts a skeleton component representing a comprehensive image structure in the input image by removing a noise component from the input image, and generates a skeleton image of being the noise removal image based on the skeleton component.

7. The detection device according to claim 1, wherein
the processor has a function to generate an attenuation factor image that represents the attenuation factor of the reflected light by brightness, using the attenuation factor, and
the processor determines whether smoke is generated in the scene to be monitored using a brightness difference between the generated attenuation factor image and a reference attenuation factor image given in advance.

8. The detection device according to claim 1, wherein, when determining that smoke is generated in the scene to be monitored, the processor outputs an alarm that reports the generation of smoke.

9. The detection device according to claim 1, wherein, when determining that smoke is generated in the scene to be monitored, the processor outputs the whole of an image including the smoke or an image part including a part in which the smoke is generated.

10. The detection device according to claim 1, wherein, when determining that smoke is generated in the scene to be monitored, the processor calculates a concentration of the smoke using the attenuation factor calculated, and outputs information on the concentration of the smoke.

11. The detection device according to claim 1, wherein the processor counts a number of pixels in which the brightness differences exceeds a predetermined first threshold, and
detects that smoke is generated in the scene to be monitored when the number of pixels exceeds a predetermined second threshold.

12. A detection method comprising:
by using a result of an image analysis of an input image that is a captured image obtained by capturing a scene to be monitored, generating a noise removal image obtained by removing a noise component from the input image;
by using brightness information included in the noise removal image, calculating an attenuation factor of reflected light from an object captured in the input image for each pixel of the input image;
generating an attenuation factor image in which the attenuation factor in each pixel is represented as brightness of the pixel; and
determining whether or not smoke is generated in the scene to be monitored based on a brightness difference between a reference attenuation factor image and the attenuation factor image, the reference attenuation factor image being an image in which the attenuation factor, which is obtained from an image captured under a situation where smoke is not generated, is represented as brightness of the pixel in each pixel.

13. A non-transitory program recording medium storing a computer program that makes a computer execute:
by using a result of an image analysis of an input image that is a captured image obtained by capturing a scene to be monitored, generating a noise removal image obtained by removing a noise component from the input image;
by using brightness information included in the noise removal image, calculating an attenuation factor of reflected light from an object captured in the input image for each pixel of the input image;
generating an attenuation factor image in which the attenuation factor in each pixel is represented as brightness of the pixel; and
determining whether smoke is generated in the scene to be monitored based on a brightness difference between a reference attenuation factor image and the attenuation factor image, the reference attenuation factor image being an image in which the attenuation factor, which is obtained from an image captured under a situation where smoke is not generated, is represented as brightness of the pixel in each pixel.

* * * * *